United States Patent
Helton et al.

(10) Patent No.: US 7,144,551 B2
(45) Date of Patent: Dec. 5, 2006

(54) MOLD REMEDIATION SYSTEM AND METHOD

(75) Inventors: Danny O. Helton, Newbury, FL (US); David W. Hobson, Boerne, TX (US); Lawton A. Seal, Schertz, TX (US)

(73) Assignee: DH Technologies, L.L.P., Boerne, TX (US)

( * ) Notice: Subject to any disclaimer, the term of this patent is extended or adjusted under 35 U.S.C. 154(b) by 651 days.

(21) Appl. No.: 10/302,696

(22) Filed: Nov. 25, 2002

(65) Prior Publication Data

US 2004/0001777 A1 Jan. 1, 2004

Related U.S. Application Data

(60) Provisional application No. 60/370,323, filed on Apr. 5, 2002.

(51) Int. Cl.
*A61L 2/20* (2006.01)

(52) U.S. Cl. .............. 422/37; 422/1; 422/28; 422/32; 422/123

(58) Field of Classification Search .............. 422/37, 422/1, 28, 123, 32
See application file for complete search history.

(56) References Cited

U.S. PATENT DOCUMENTS

| | | | |
|---|---|---|---|
| 2,126,958 A * | 8/1938 | Guha | 426/318 |
| 4,033,871 A | 7/1977 | Wall | 210/96 R |
| 4,084,747 A | 4/1978 | Alliger | 239/4 |
| RE31,779 E | 12/1984 | Alliger | 252/187.23 |
| 4,741,858 A | 5/1988 | Choy et al. | 252/186.36 |
| 4,880,638 A | 11/1989 | Gordon | 424/662 |
| 5,141,652 A | 8/1992 | Moore, Jr. et al. | 210/754 |
| 5,314,719 A * | 5/1994 | Batdorf et al. | 427/385.5 |
| 5,643,861 A | 7/1997 | De Guertechin et al. | 510/365 |
| 5,820,822 A | 10/1998 | Kross | 422/37 |
| 6,116,254 A | 9/2000 | Shiramizu | 134/99.1 |
| 6,162,371 A | 12/2000 | Rees et al. | 252/187.22 |
| 2002/0014178 A1 | 2/2002 | Haught et al. | 106/15.05 |
| 2002/0072288 A1 | 6/2002 | Hei et al. | 442/59 |
| 2003/0143111 A1 * | 7/2003 | Cowley et al. | 422/37 |

\* cited by examiner

*Primary Examiner*—Krisanne Jastrzab
*Assistant Examiner*—Sean E. Conley
(74) *Attorney, Agent, or Firm*—Christopher J. Whewell

(57) ABSTRACT

Provided herein are systems and methods associated therewith for killing molds and reducing other contaminating bioburden that may include bacteria and their spores, yeast, and viruses within various dwellings including homes, office buildings, institutions, and any other enclosed space in which humans reside, either temporarily or permanently. The technology of the present invention can be used to treat vehicles, airplanes, and ships. A process according to the invention includes the generation of a gaseous oxyhalogen species and distribution of the gaseous oxyhalogen species throughout a selected dwelling. It has been unexpectedly found that the concentration level of gaseous oxyhalogen species necessary to kill molds according to the inventive methods is far below that previously recognized in the art as being necessary for the killing of such molds. Thus, mold infestations may be killed in dwellings with minimal disruption to the usual business of the inhabitants. Further, fabrics such as drapes and upholsteries contained within such dwellings may be carried out without causing any detrimental color changes to the fabrics.

Figure 1:
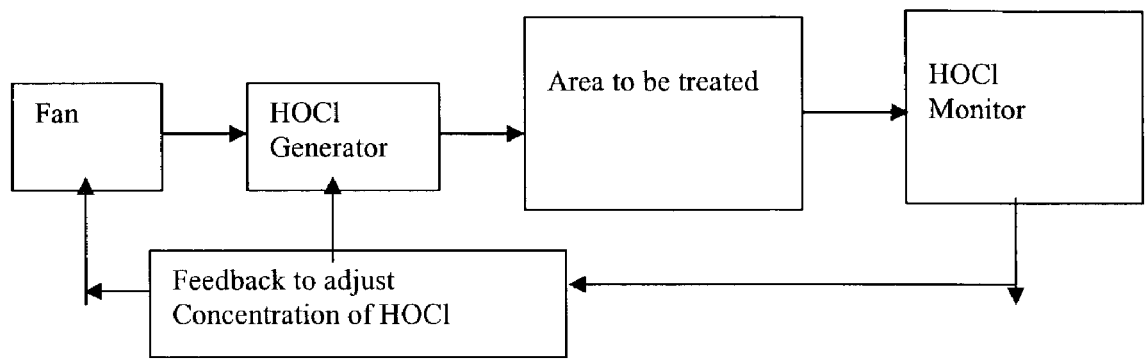

22 Claims, 1 Drawing Sheet

# MOLD REMEDIATION SYSTEM AND METHOD

CROSS-REFERENCES TO RELATED APPLICATIONS

This application claims the benefit of U.S. Provisional Application No. 60/370,323 filed Apr. 5, 2002, the entire contents of which are herein incorporated by reference.

TECHNICAL FIELD

This invention relates generally to a system useful in mold remediation, and methods associated with its use. More particularly, it relates to a system for treating rooms, ducts, and other confined areas and surfaces which are contaminated with various molds using a volatile oxyhalogen species.

BACKGROUND INFORMATION

Members of the Kingdom Fungi obtain their nutrition from organic carbon sources. The body of a fungus secretes enzymes which degrade the organic substrate on which they are growing, to yield smaller entities, which are in turn absorbed into the body of the fungus and are metabolized to provide energy to carry on its vital life processes. Molds are one manifestation of fungi which can present serious health problems to mammals because they produce dangerous mycotoxins, which are in general neurotoxins, and some of which have been found to be carcinogenic. Mycotoxins are chemical substances created by various molds generally as secondary metabolites, which are theorized to possibly play a role in either helping to prepare the substrate on which they exist for digestion, or as a defense mechanism. It has also been suggested by some that mycotoxins may be produced when the organisms are under stress, which could be related to competition/defense, or simply due to inhospitable environmental conditions. Regardless of their true biological function, the mycotoxins are a recognized health hazard.

Mycotoxins most commonly reach people from the air, via spores from an infestation of mold. Mycotoxins are also found at times in small particulates, which may comprise mold dust, which is comprised of small particles of mold that have dried. Mold spores, when inhaled, can begin to colonize in the sinuses and throughout the body, including the brain, lung, and intestinal tract, and after a period of time may lead to serious health effects.

One of the mycotoxins, aflatoxin, is produced by the fungi *Aspergillus flavus* and *Asperfillus parasiticus*. Four different aflatoxins denoted as B1, B2, G1 and G2, have been identified with B1 being the most toxic, carcinogenic and prevalent. In addition to other toxic characteristics, aflatoxin interferes with the immune system's ability to produce gamma globulin, a protein that is part of the host defense mechanism. The resulting breakdown of the immune system renders animals that have ingested such mold vulnerable to a variety of diseases.

Another very dangerous family of toxin producers is Fusarium. The toxins zearalenone, trichothecenes or moniliformin can be formed by various types of *Fusarium* including *F. moniliforme, F. oxysporum, F. culmorum, F. avenaceum, F. equiseti, F. roseum*, and *F. nivale*. In addition, under certain growth and environmental conditions, *Stachybotrys chartarum* may produce several different mycotoxins, including a very strong class known as trichothecenes. Trichothecenes are also produced by several common molds including species in the genera Acremonium (Cephalosporium), Cylindrocarpon, Dendrodochium, Myrothecium, Trichoderma, and Trichothecium. The trichothecenes are potent inhibitors of DNA, RNA, and protein synthesis, and have been well studied in animal models because of concern about their potential misuse as agents of biological warfare, due to their ability to destroy human health (mentally and physically), and never show up in an autopsy. Thus, infested homes and buildings are one of the major causes of fungal illness in industrialized nations today.

Mold requires a compatible temperature for each species. Some molds are cryophytes, which means that they favor to low temperatures for best growth, while others are thermo tolerant and adapt to a wide range of temperatures. Others still are thermopiles, and require higher temperatures for best growth. Depending on the species, these microbes can grow just about anywhere. Environmental factors (temperature, nitrogen, oxygen, etc.) provide the necessary conditions for indoor molds to thrive.

Molds need an organic source of food. It is surprising to some to see molds growing on glass, tile, stainless steel, cookware, etc.; however, such molds are in fact feeding off of some organic source deposited on these substrates (oils, films, dirt, skin cells, etc.). The fiberglass insulation that many manufacturers claim that mold does not grow on their product is a fairly true statement, however, molds nevertheless do grow on such substrates and molds disposed on such fiberglass actually thrive on organic debris that is entrapped within the interstices between the compressed fibers and on their surfaces. Mold also grows on things such as wood, fabric, leather, gypsum, fiberboard, drywall, stucco, and many insulation fibrous materials.

All molds require some form of moisture to grow; however, like temperature, the amount of moisture varies for different species. Some are xerophillic and colonize under very dry conditions, some are xerotolerant and colonize under a wide range of moisture levels, and some are hydrophilic and colonize at high moisture levels. Humidity or moisture content of the substrate can often be sufficient at levels as low as 50% relative humidity to create conditions which are problematic in many indoor environments. Thus, mold colonies can spread very easily through any HVAC system, often thriving on the surface of insulations, owing to the presence of organic matter such as sebum, dust, old spiderwebs, insect corpses, or basically any extraneous organic matter. Because of the capability of molds to thrive within heating and air conditioning ducts, or behind common drywall where moisture is present, mycotoxins may be produced within a dwelling unbeknownst to the inhabitants and distributed within the living space. When mycotoxins are produced at levels below the threshold for clinical manifestations, they may not exhibit any acute effects on the inhabitants, but rather effects over time are due to chronic persistent exposure, which may not be readily ascribed to their source. When mycotoxins are produced at or above the clinical threshold, leading to immediately recognizable adverse effects on health, it is quite common for an entire dwelling such as a home or urban building to be totally uninhabitable. In such instances, drastic measures are needed if the toxins are to be remediated. In extreme cases, demolition of the structure by razing with fire has been the means prescribed for eradicating the infestation. Owing to the magnitude of the problem of mold infestations, the efforts of several workers in the prior art have been directed at antifungal compositions and methods for their use. Typically, antimicrobials function as antifungal as well. For example, U.S. Pat. No. 4,084,747 discloses a process for the production of a composition having germicidal properties comprising contacting sodium chlorite with a substantially water soluble acid material selected from the group consisting of: organic acids and mixtures thereof with inorganic acid, wherein the contacting is carried out in aqueous media and in the presence of sufficient of the acid to lower the pH of the aqueous media to less than about 7. Further, the contacting may be carried out using ultrasonic means. This patent also provides a process for disinfecting and sterilizing which comprises contacting a germ carrier with at least a small but effective germ-killing amount of a germicidal composition obtained by reacting sodium chlorite with a substantially water soluble acid material selected from the group consisting of: organic acid and mixtures thereof with inorganic acid, the acid material comprising at least about 15% by weight of lactic acid and wherein the contacting is carried out in aqueous media and in the presence of sufficient of the acid to lower the pH of the aqueous media to less than about 7. U.S. Reissue Pat. No. 31,779 provides a germ-killing composition produced by contacting an acid material, preferably consisting of at least about 15% by weight of lactic acid, with sodium chlorite in aqueous media, the amount of acid being sufficient to lower the pH of the aqueous media to less than about 7. Methods of disinfecting and sanitizing include application of either the germ killing composition, or reactants providing in situ production thereof, to a germ carrier including substrates of various kinds as well as an enclosed air space. U.S. Pat. No. 4,880,638 teaches a biocidal composition comprising water, a source of chlorite ions, a source of chloride ions and a source of chlorate ions where the molar ratio of chlorite ions to chlorate ions is in the range from about 2:1 to about 1000:1, the mole ratio of chlorite ions to chloride ions is from about 0.1:1 to about 1000:1 and the mole ratio of chloride ions to chlorate ions is in the range from about 0.1:1 to about 1000.1; the chlorite ion source present in amounts of from about 40 grams to about 0.04 milligrams per thousand grams of water; and the composition including a pH adjusting material in an amount sufficient to adjust the pH of the mixture to above 7.0. A composition according to this invention avoids the formation of significant amounts of chlorine dioxide. U.S. Pat. No. 5,141,652 sets forth a process for reducing biological activity in a water system which process comprises: a) providing a supply of a biocidal solution, which solution comprises: (i) bromine chloride (BrCl), (ii) water, (iii) and a sufficient amount of a stabilizer consisting essentially of a halide salt or a hydrohalic acid or a mixture of halide salt and hydrohalic acid such that less than 30% of the BrCl reacts with water per year to form hypobromous acid and hydrochloric acid; and b) adding from the supply, the biocidal solution to the water system at a rate sufficient to maintain at least about 1 to 2 parts of hypobromous acid per million parts of water. U.S. Pat. No. 5,820,822 teaches compositions and methods for creating disinfecting and deodorizing chlorous acid, $HClO_2$ and chlorous-acid derived oxychlorine species from metal chlorite salts without utilizing proton-donating acids. The chlorous acid in aqueous solutions provides its oxidative disinfecting and deodorizing action through a series of transient and stable oxychlorine degradation species. These include hypochlorous acid HOCl, dichlorine dioxide $Cl_2O_2$, and chlorine dioxide $ClO_2$. The chlorine dioxide/chlorite complex anion $Cl_2O_4$ is also believed to provide antimicrobial and deodorizing properties. U.S. Pat. No. 6,116,254 discloses a cleaning system for a semiconductor substrate comprising: a) a cleaning tank in which a cleaning action on a semiconductor substrate is performed; b) a pure water supplying system for supplying pure water to the tank; and c) a chlorine gas supplying system for supplying a chlorine gas to the pure water existing in the tank so that the chlorine gas reacts with the pure water in the tank to generate $ClO_x$ ions, whereby the pure water containing the $ClO_x$ ions can be used as a cleaning solution for the semiconductor substrate placed in the tank. U.S. Pat. No. 6,162,371 discloses a stabilized acidic bleaching composition comprising an admixture of: a) a bleaching source of monopositive chlorine ion; b) a chlorine stabilizing agent selected from the group consisting of sulfamic acid, alkyl sulfamates, cycloalkyl sulfamates, aryl sulfamates and melamine; c) an acidic buffer present in an amount effective to provide the bleaching composition with a pH in a range of about 2 to about 6.5, wherein the acidic buffer comprises a weak acid and a salt of the weak acid; and d) water, wherein the molar ratio of chlorine stabilizing agent to the monopositive chlorine ion in the composition is greater than about 1:1. US Patent Application 2002/0072288 provides a method for antimicrobial treatment comprising applying to microbes a composition containing a diluting solvent, an antimicrobially-active solvent having a density different from the density of the diluting solvent, and an optional cosolvent, surfactant, or additional antimicrobial agent, wherein the amount of antimicrobially-active solvent or additional antimicrobial agent is sufficiently high and the amount of co-solvent or surfactant is sufficiently low so that the composition will provide greater than a 1-log order reduction in the population of spores or bacteria of Bacillus cereus within 10 seconds at 60 degrees C.

Thus, the prior art is replete with compounds and solutions of compounds useful for destroying fungi and various microbes, including the foregoing, and many other compositions and processes described in the literature. However, in cases where it is desired to eradicate a mold colony which is releasing harmful quantities of mycotoxins into an indoor environment, there exists at present no simple manner of treating such molds to their detriment without resorting to extreme techniques, especially for cases where molds are not directly accessible for physical removal. Effective methods for eradicating hidden molds include tearing into walls and dismantling ventilation systems. However, these methods are not only labor-intensive, but they also generally require the area being remediated to be evacuated during the remediation process. In addition to the loss of use of such environments being treated being inconvenient, current extreme remediation methods are expensive.

The present invention provides a method for severely inhibiting or eradicating the growth of molds from locations where molds thrive, without the need for dismantling air distribution systems or destroying the structural components of dwellings, such as walls. A method according to the invention is cost-effective and relatively non-labor intensive, as it is administered with all building systems intact. All parts and percentages stated herein are expressed on a weight basis, unless otherwise specified.

SUMMARY OF THE INVENTION

One aspect of the present invention is a process for killing molds and reducing other contaminating bioburden that may include bacteria and their spores, yeast, and viruses which comprising the steps of: a) providing a vessel (the "generation vessel") containing an aqueous solution at a first pH level from which a gaseous oxyhalogen species may be evolved upon adjustment of the aqueous solution to a second pH level; and b) adjusting the pH of the aqueous solution from the first pH level to a second pH level so as to cause vapors comprising an oxyhalogen species to be evolved from the solution; and c) causing an air current to exist in the ambient surroundings of the vessel from which the vapors are evolved so as to provide an air stream which contains a gaseous oxyhalogen species; and d) directing the flow of the air current to a location at which a mold colony is growing for an effective amount of time to kill the mold.

The invention also provides a system useful for treating a dwelling to kill molds wherein the system comprises: a) a vessel containing an aqueous solution at a first pH level from which a gaseous oxyhalogen species may be evolved upon adjustment of the aqueous solution to a second pH level; and b) a microprocessor means; and c) a means for altering the pH of the contents of the vessel from the first pH level to the second pH level, so as to cause evolution of a gaseous oxyhalogen species from the aqueous solution; and the means for altering is in effective electrical contact with the microprocessor means. In this embodiment there is also provided a means for directing the gaseous oxyhalogen species from its point of evolution from the aqueous solution to a second pre-selected location; and a means for monitoring the concentration of the gaseous oxyhalogen species at the second pre-selected location, wherein the means for monitoring is in effective electrical contact with the microprocessor means.

According to yet another aspect of the invention there is provided a system useful in remediating toxic molds from houses and other dwellings which comprises: a) an oxyhalogen generator means for providing a volatilized oxyhalogen species; and b) a distribution means for distributing the volatilized oxyhalogen species so as to provide an oxyhalogen-enriched atmospheric zone; c) a means for monitoring the concentration of the oxyhalogen in the oxyhalogen enriched zone and d) a means for providing feedback derived from the means for monitoring, back to the oxyhalogen generator means.

According to yet another embodiment, the invention provides a process for killing molds and reducing other contaminating bioburden that may include bacteria and their spores, yeast, and viruses comprising the steps of: a) providing a vessel containing an aqueous solution at a first pH level from which a gaseous oxyhalogen species may be evolved upon adjustment of the aqueous solution to a second pH level; b) adjusting the pH of the aqueous solution from the first pH level to a second pH level so as to cause vapors comprising an oxyhalogen species to be evolved from the solution, and thus forming an actively-evolving solution; c) vaporizing the actively-evolving solution using a mechanical means selected from the group consisting of: spray misters, ultrasonicators, and high-pressure venturi evaporators, to form a cidal vapor; d) causing an air current to exist in the ambient surroundings of the cidal vapor so as to provide an air stream which contains a gaseous oxyhalogen species; and e) directing the flow of the air current to a location at which a mold colony is growing for an effective amount of time to kill the mold.

BRIEF DESCRIPTION OF DRAWINGS

In the annexed drawing:

FIG. 1 is a diagram of a feedback control scheme useful in accordance with an embodiment of the present invention.

DETAILED DESCRIPTION

According to the present invention, an oxyhalogen species is generated and is subsequently distributed throughout the atmosphere inside of a dwelling, which dwelling contains surfaces that are exposed to the atmosphere and are infested with a mold. As used in this specification and the appended claims, the words "oxyhalogen species" means any chemical compound, molecule, ion, complex, or species having an oxygen atom that is chemically bonded to a halogen atom. Examples of oxyhalogen species include, without limitation, hypochlorous acid, chlorous acid, chloric acid, perchloric acid, hypobromous acid, bromous acid, bromic acid, perbromic acid, hypoiodous acid, iodous acid, iodic acid, periodic acid, chlorine monoxide, chlorine dioxide, chlorine heptoxide, and all other known oxides of elemental halogens.

The halogens are a well known class of elements of the periodic table of the elements and include fluorine, chlorine, bromine, iodine, and astatine. Owing to the radioactivity of astatine, this element does not find the widespread use as the remainders of the halogens. Also, owing to the peculiar chemical nature of fluorine and its compounds, and its relatively high cost with respect to the remaining halogens, it too finds less widespread use in similar employments of the remaining three halogens. Of the three remaining, chlorine, bromine, and iodine, chlorine is the one which is in greatest use, by far for most industrial applications, owing to its being plentiful and easily refined.

The halogens are well-known to chemists to share many of the same chemical properties with one another to a larger degree than is seen in the behavior of other families of elements in the periodic table. Thus, it is in general true that the chemistry of one halogen is typically applicable to the remaining. For the case of chlorine, dissolution of chlorine in water is described by the following equilibrium expression:

$$Cl_2+H_2O \rightarrow HCl+HOCl \quad (I)$$

This action proceeds to completion in the presence of mercuric oxide, which removes both protons and chloride ion. The mercuric chloride is precipitated as the basic chloride HgO, $HgCl_2$, which together with the excess of mercuric oxide may be filtered off, and the resulting filtrate distilled. If a 25% aqueous solution of hypochlorous acid is distilled at a low pressure, pure chlorine monoxide is evolved, which is a gaseous oxyhalogen species. If a more dilute solution is distilled, the distillate is an aqueous solution of hypochlorous acid, which is also an oxyhalogen species for purposes of the present invention.

Thus, one of the simplest methods of producing an oxyhalide species is to simply bubble chlorine gas into water, to yield a solution of hypochlorous acid and hydrochloric acid, both aqueous when an excess of water is present. Alternatively, aqueous solutions of ionic oxyhalogen species from which a gaseous species of an oxyhalogen compound may be evolved upon the addition of acid thereto may be prepared by the electrolysis of an alkaline solution of halogen ions, such as by the electrolysis of alkaline solutions of sodium chloride to form a sodium hypochlorite solution. Subsequent sufficient acidification of an alkaline aqueous sodium hypochlorite solution yields aqueous hypochlorous acid, which is an oxyhalogen species. Hypochlorous acid is then liberated from the solution, which solution may be considered to be an actively-evolving solution. Since hypochlorous acid is only known in solution, and the pure acid has never been isolated, when hypochlorous acid is selected as the desired gaseous oxyhalogen species to be used to eradicate a mold colony according to the invention, it is most preferred to begin with a solution of hypochlorite ions and acidify such solution so as to cause evolution of hypochlorous acid therefrom. It is most probably true that molecules of hypochlorous acid are stable only when associated with water molecules, which presumably inhibit the decomposition of the hypochlorous acid into water, oxygen, and chlorine, depending upon the conditions of the decomposition and the presence or absence of other elements and compounds.

According to one simple embodiment, the invention comprises a means for generating an oxyhalogen species, a means for volatilizing the oxyhalogen species so generated, and contacting a mold colony with an effective amount of the volatilized oxyhalogen species for inhibiting growth of, and preferably killing, the mold and reducing other contaminating bioburden that may include bacteria and their spores, yeast, and viruses. A crude manifestation of the present invention is thus represented by a beaker of a solution of a hypochlorite salt which has been acidified to a pH of about 6.0 so as to cause formation of hypochlorous acid in the solution and headspace above the liquid; and an air circulating means, such as a fan, whose flow is directed over the top of the beaker so as to cause vapors of aqueous hypochlorous acid to be directed out of the beaker and into the surrounding airspace, wherein the airspace is in contact with a mold colony.

Thus, one element of the present invention is a means for directing the flow of gases evolved from a vessel (in which is contained a chemical species from which a gaseous oxyhalogen species may be evolved subsequent to its acidification) from their point of generation to a selected second location. Often, the second location is merely the contents of a home or office building, and the point of evolution is within a duct of an HVAC system, and the means for circulating the air comprises a fan means, as such are known to those skilled in the art. However, the means for generation or distribution of vapors of a gaseous oxyhalogen species according to the invention may also include those means known in the art in evaporative decontamination systems, forced evaporation conditions using an ultrasonicator, or a high pressure venturi evaporator. By use of an ultrasonicator or high pressure venturi evaporator it is possible to also add an agent, other than the oxyhalogen species, that can be deposited on the surfaces being treated to retard growth of microbes. To be useful in this regard, the agent should not be too volatile, (i.e., having a boiling point of greater than about 180 degrees Centigrade at standard conditions of temperature and pressure) while having good antimicrobial properties, and must not be reactive with other components in the formulation. Examples of suitable antimicrobials include, without limitation: quaternium compounds such as benzalkonium chloride and bromide; benzethonium chloride; polyquaternium 1; aliphatic alcohols having any number of carbon atoms less than about 20 that meet the boiling point requirement, whether straight chain or branched; benzoic acid and its salts and esters; phenols; mono- and poly-hydroxy benzoic acids, their salts, and esters; sorbic acid and its salts and esters; mono- and polycarboxylic acid and their salts that meet the boiling point requirements, 3,3'-dibromo-4,4'-hexamethylene-dioxydibenzamidine and its salts; undec-10-enoic acid and its salts; triclocarban (INN); alkyl $C_{12}$–$C_{22}$ trimethyl ammonium bromide and chloride; and saccharinate. These may be added directly to the solution from which the gaseous oxyhalogen species is evolved and sprayed or otherwise vaporized and distributed through a selected volume within a living space.

Aqueous solutions of hypochlorites are known to have anti-microbial effects. However, the concentration level at which aqueous hypochlorite solutions have been recognized and specified in the prior art as being useful for killing germs on surfaces is on the order of 200 ppm in aqueous solutions, as stated on the label of the commercial product known as Ultra CloroX™ from the Clorox Company. A concentration of 200 ppm sodium hypochlorite corresponds to $200 \times 10^{-6}$ grams/cc. However, the prior art contains no specification for using vapors comprising hypochlorous acid for remediating molds or otherwise treating microbes.

Hypochlorous acid in the vapor form can decompose to form some chlorine gas. The current ACGIH short term exposure limit (TLV-STEL) for chlorine gas is 1 ppm (2.9 $mg/m^3$). The present invention however eliminates this decomposition by careful pH maintenance of the generating solution and vapor at levels that are not conducive to decomposition and production of chlorine gas. Under some conditions, high concentrations of hypochlorous acid has been known to act as a corrosive agent and chemical irritant; however, at the concentrations controlled by microprocessor in accordance with the invention, potential harmful effects to humans or animals may be significantly reduced or eliminated altogether. In controlling the pH and generation of hypochlorous acid vapor it has been discovered unexpectedly that the actual effective concentration level at which vapors of hypochlorous acid can kill or remediate mold colonies are on the order of about 5 micrograms per cubic centimeter of air. In controlling the pH and generation of hypochlorous acid vapor it has been discovered unexpectedly that the actual effective concentration level at which vapors of hypochlorous acid can kill or remediate mold colonies are on the order of about 5 micrograms per cubic centimeter of air or less. This is a concentration that is controlled such that the vapor is maintained and controlled precisely. Cidal action against mold and other contaminating bioburden which may include bacteria and their spores, yeast, and viruses can be accomplished at controlled conditions allowing the exposure to the system operator to be below that at which the material is harmful to humans over the short term of exposure necessary to kill the mold colonies. We have also found that in most, if not all cases, it is possible to completely eradicate even the most refractory of mold colonies in 24 hours or less using hypochlorous acid vapors generated and controlled as described herein.

According to a preferred form of the present invention, an aqueous solution which contains hypochlorite ions is adjusted to have a pH sufficient to cause formation of substantial amounts of free hypochlorous acid, which owing to its volatility is evolved from the solution into the surrounding atmosphere of the vessel in which such solution is contained. Hypochlorous acid dissociates as pH increases according to the well known equation:

$$HOCl \rightarrow H^+ + OCl^- \text{ pH increase} \qquad (II)$$

Similarly if the pH decreases hypochlorous acid dissociates as follows:

$$HOCl + HCl \rightarrow Cl_2 + H_2O \text{ pH decrease}$$

The equilibrium constants controlling these reactions at 25° are:

$K_1 = ([HClO][Cl^-][H^1])/[Cl_2] = 4.5 \times 10^{-4}$ $K_2 = ([ClO^-][H^1])/[HOCl] = 2.7 \times 10^{-8}$ As with all acid dissociations, the dissociation between HOCl and ⁻OCl is reversible, and pH driven. As HOCl is consumed, OCl⁻ shifts back to HOCl to maintain the pH mandated equilibrium. Representative pH levels and their corresponding percentages of HOCl and OCl⁻ are:

| pH | % as HOCl | % as OCl— |
|---|---|---|
| 8.0 | 22 | 78 |
| 7.8 | 33 | 67 |
| 7.5 | 48 | 52 |
| 7.2 | 66 | 34 |
| 7.0 | 72 | 28 |
| 6.0 | 96 | 4 |
| 5.0 | 100 | 0 |

At a pH of greater than about 5.5 essentially all of the chlorine is converted to hypochlorous acid and on to hypochlorite ion. A working pH of >=5.5 is preferred to avoid formation of chlorine gas.

Teachings in the prior art of cleansing formulations warn household consumers against mixing acids with bleach solutions, because bleach solutions contain about 5 to 6% by weight of hypochlorite, and acidifying such solutions results in the evolution of chlorine gas and other gaseous species which can cause serious health effects. In fact, chlorine gas has been used as a chemical warfare agent. However, by careful control of the pH of the aqueous solution which contains hypochlorite ions, we have found it to be possible to predominantly cause only the beneficial evolution of hypochlorous acid vapors from the solution for the purpose contemplated by the present invention, without the evolution of deleterious amounts of chlorine and other gases. In such gaseous state, the vapor form of hypochlorous acid has excellent penetrating and diffusion characteristics for rapid and effective treatment of furnishings and HVAC systems.

Thus, a central aspect of the use of a process according to the present invention is the aqueous solution from which a gaseous oxyhalogen species may be evolved, when it is desired to evolve such gaseous oxyhalogen species. In general terms, such an aqueous solution contains as a main ingredient a chemical species capable of generating an oxyhalogen compound which is volatile at the temperatures encountered. According to one preferred embodiment of the invention, such an aqueous solution contains hypochlorite ions, at a pH level at which hypochlorite ions are stable, which is generally any pH above about 8.0. When practicing a process according to the invention, the pH of such a solution is adjusted downward, preferably using aqueous acid, to cause the evolution of the oxyhalogen species, which according to a preferred form of the invention is hypochlorous acid vapor. However, aqueous solutions of other ionic species which are stable and do not evolve a gaseous oxyhalogen species until their pH is adjusted towards the acid side of neutrality are also useful in accordance with the invention, including hypoiodite ions, hypobromite ions, chlorite ions, bromite ions, iodite ions, etc.

For the sake of stability of the aqueous solution from which a gaseous oxyhalogen species is to be evolved in accordance with the invention, it is preferred that the aqueous solution contain a pH buffer. The buffer chosen is not critical as long as the proper pH is maintained and the acidifier that is added to the solution from which a gaseous oxyhalogen species such as hypochlorous acid, does not react with HOCl. Any buffer known to those skilled in the art may be used for this purpose, with the main proviso for suitability being that the components of such buffer must be relatively stable towards the ionic species from which the gaseous oxyhalogen compound is derived and the gaseous oxyhalogen species itself. Suitable buffer systems thus include without limitation: phosphate buffers; sulfate buffers; acetic/acetate buffers; $C_1$–$C_{10}$ mono- and polycarboxylic acid buffers; substituted carboxylic acids such as lactic, ascorbic, and tartaric acid buffers; and carboxylic acids that have unsaturation such as maleic and furmaric buffers. The present invention contemplates use of all buffer systems known to those skilled in the art. Buffer systems are known to contain salt pairs. Currently, the most preferred buffer is acetic acid, adjusted to a pH of about 6.0 to 6.5.

We have unexpectedly found that the concentration levels of gaseous oxyhalogen species which are useful for killing molds and reducing other contaminating bioburden that may include bacteria and their spores, yeast, and viruses according to the invention is far below those levels normally recommended by those in the art as being necessary for killing microbes, including molds, fungi, and the like. Subsequent to our learning this, we have come to the realization that the use of a process and system according to the invention will not unduly corrode existing ventilation systems and their associated hardwares which are subjected to a process according to the invention. Nevertheless, the present invention contemplates the inclusion of corrosion inhibitors in the aqueous solution from which the gaseous oxyhalogen species is to be evolved in accordance with the invention. It is preferred that corrosion inhibitors for use in the present invention be volatile, and may be readily vaporized along with the gaseous oxyhalogen species, in order to exert a protective effect on metals in particular into which they come into contact with. The use of mechanical means such as spray misters, ultrasonicators, and high-pressure venturi evaporators are beneficial to readily vaporize solutions containing an oxyhalogen species and a corrosion inhibitor together. Examples of corrosion inhibitors suitable for use as a component of a solution from which an oxyhalogen species is evolved in a process according to the invention include without limitation: di(alkali metal)phosphate and mono(alkali metal) phosphate. In some instances it may be desirable to coat metal surfaces such as copper or aluminum with a corrosion inhibitor before exposing to oxyhalogen species. The present invention contemplates the use of other corrosion inhibitors as well, wherein the corrosion inhibitor may be housed in the same vessel from which the oxyhalogen species is evolved, or may be contained in a separate vessel, and is vaporized using a separate means (mechanical or otherwise) for vaporizing than is used for the vaporization of the oxyhalogen species. Examples of corrosion inhibitors suitable for use not in a solution of oxyhalogen species include: di(alkali metal)phosphate, mono(alkali metal) phosphate, N,N'-dimethylethanolamine, morpholine, 2-mercaptobenzothiazole, 2,5-dimercapto-1,3,4-thiadiazole, sodium or potassium tolyltriazole, tolyltriazole, carboxybenzotriazole, quaternized imino imidazolines and quaternized amido imidazoles.

According to a process of an embodiment of the invention, there is provided a vessel containing an aqueous solution of ionic species which exists at a first pH level from which a gaseous oxyhalogen species may be evolved upon adjustment of that aqueous solution to a second pH level, and adjustment is made to the pH of that aqueous solution from the first pH level to a second pH level so as to cause vapors comprising an oxyhalogen species to be evolved from the solution. Adjustment of the aqueous solution may be effected by manually adding a solution of an aqueous acid, (including those such as those selected, without limitation, from the group consisting of: hydrochloric acid, sulfuric acid, nitric acid, phosphoric, acetic, formic, sulfurous, phosphorous, nitrous, perchloric, chloric, hydriodic, hydrobromic, benzenesulfonic acid, citric acid, fumaric acid, glycolic acid, lactic acid, malic acid, maleic acid, tartaric acid, propionic acid, acetic acid, mandelic acid, sodium bisulfate, potassium bisulfate, phosphoric acid, and mixtures of any of the foregoing with one another) to the vessel which contains the ionic oxyhalogen species. Alternatively, adjustment of the aqueous solution may be effected automatically by means of an automatic titrator or "autotitrator" as such devices are known to those skilled in the art. A suitable automatic titrating burette is marketed by Brinkmann and designated Metrohm Dosimat® 665. Any electronically actuated burette capable of metering a specific amount of an acidic aqueous solution is suitable for use in the present invention.

In FIG. 1 is depicted a schematic representation in block diagram form of an alternate embodiment of a process according to the invention. In this figure, the HOCl generator may comprise an acidified hypochlorite solution in a vessel, which emits vapors that are directed by the fan means to the area to be treated, which may include rooms, ducts, etc. There is a monitoring means which provides feedback to the microprocessor, which in turn controls the acidification rate and level of the HOCl generator. Alternatively, the feedback may control the mechanical means for generating HOCl vapor, when such embodiment is employed.

The present invention has the added advantage in that surfaces which may not normally be treated using a bleaching solution of hypochlorite ions, such as fabrics including drapes, curtains, and upholstery may be successfully treated according to the present invention without causing damage to the fabric or color alteration (bleaching out).

If desired, the system of the invention can be provided with means for recording various concentrations, so that the course of changes in gaseous oxyhalogen species and halogen or other chemical species in the air can be followed. This information can be useful to reveal faulty operation in some part of the circulation system, such as, for example, faulty excessive or insufficient halogen or alkali or acid feed to the gas generation vessel. Alarm circuits can also be included, which give an alarm when either pH of the generation vessel or gaseous oxyhalogen species content or both fall outside the prescribed ranges.

Sanitation of Surfaces Using Sodium Hypochlorite

First, the recommended concentration of HOCl for sanitization of surfaces according to the prior art is calculated. Referring to the label of Ultra Chlorox® brand of sodium hypochlorite and noticing that a recommended concentration of NaOCl for sanitation is 200 parts per million. The maximum concentration of HOCl from this solution after pH adjustment is:

200 ppm NaOCl=0.0200 g NaOCl/100 ml=0.0200 g NaOCl/100 cc 0.0200 g NaOCl/100 cc=(0.0200 g NaOCl)(52.5 g HOCl)/74.5 g NaOCl)/100 cc =0.0141 g HOCl/100 cc=0.000141 g HOCl/cc =$1.41 \times 10^{-4}$ g HOCl/cc Ultra Chlorox® brand of sodium hypochlorite is shipped at a pH of >10 for stability purposes. When it is diluted for use the pH will drop by varying amounts depending on water source. Thus, according to the prior art recommendation by the manufacturer of Chlorox® bleach, the equivalent concentration of HOCL necessary to sanitize is $1.41 \times 10^{-4}$ g HOCL/cc.

According to our invention, we have found that vapor from a suitably acidified NaOCl sample is appropriate to kill mold when the ratio of the volume of the solution to gas volume is as now set forth below. For purposes of the calculation which now follows, it is assumed that essentially all of the NaOCl is converted to HOCl when acidified, which is a valid assumption given the equilibrium of the reaction. For mold remediation studies, 10 ml of acidified 600 ppm NaOCl was placed in a container with a volume of 1400 cc.

10 ml of 600 ppm NaOCl=0.00600 g NaOCl/10 ml 0.00600 g NaOCl=(0.00600 g NaOCl)(52.5 g HOCl)/(74.5 g NaOCl)=0.00423 g HOCl This quantity is diluted to 1400 cc.

Therefore, the maximum concentration of HOCl gas in the container studied is:

0.00423 g/1400 cc=$3.02 \times 10^{-6}$ g HOCl/cc.

Next, we examined the ratio of recommended hypochlorite concentration in solution to hypochlorite concentration in gas that we have found to be effective to kill mold, which is simply the quotient:

($1.41 \times 10^{-4}$ g HOCl/cc)/($3.02 \times 10^{-6}$ g HOCl/cc)=46.7.

Thus, we have discovered that by converting the NaOCl to HOCl and using it in the form of a gas the concentration needed for mold cidal activity is at least about 47 times less than is recommended for sanitation in the liquid form of hypochlorite bleach! We next investigated the removal of mold stain from surfaces.

Removal of Mold Stain from Surfaces

First, the recommended concentration of HOCl for sanitization of surfaces according to the prior art is calculated. Referring to the label of Ultra Chlorox® brand of sodium hypochlorite and noticing that a recommended concentration of NaOCl for mold and mildew stain removal is ¾ cup Ultra Chlorox® plus one gallon of water. Ultra Chlorox® contains 6.00% NaOCl per the label. For purposes of the calculation which now follows, it is assumed that all of the NaOCl is converted to HOCl when diluted for use.

(¾ cup)(8 ounces/cup)(28.5 g/ounce)=171 g (weight of Ultra Chlorox®)

(171 g Ultra Chlorox®)(0.06 g NaOCl/g Ultra Chlorox®)= 10.3 g NaOCl (1 gallon)(4 quarts/gallon)(32 ounces/quart)(28.5 g/ounce)= 3648 g Total weight of recommended solution for mold stain removal=171+3648=3819 g NaOCl conc. recommended by Ultra Chlorox®=10.3 g/3819 cc=0.00270 g/cc Conc. of HOCl=(0.00270 g/cc)(52.5 g HOCl)/(74.5 g NaOCl)=0.00190 g HOCl/cc =$190 \times 10^{-5}$ g/cc We have found that vapor from a suitably acidified NaOCl sample is appropriate to kill mold and remove stains when the ratio of the volume of the solution to gas volume is as shown below. For the mold remediation studies, 5 mL of 6.0% NaOCl was mixed with 50 mL of water, acidified and was placed in a container with a volume of 1400 cc.

5 mL of 6.0% NaOCl=0.30 g NaOCl

Assuming all of the NaOCl is converted to HOCl:

0.30 g NaOCl=(0.30 g NaOCl)(52.5 g HOCl)/(74.5 g NaOCl)=0.21 g HOCl

This quantity of HOCl is diluted to 1400 cc. Therefore, the maximum concentration of HOCl gas in the container studied is:

0.21 g HOCl/1400 cc=15×10$^{-5}$ g HOCl/cc

Next, we examined the ratio of recommended hypochlorite concentration in solution to hypochlorite concentration in gas that we have found to be effective to remove mold and mildew stains from substrates, which is simply the quotient:

(190×10$^{-5}$ g/cc)/(15×10$^{-5}$ g HOCl/cc)=13

Thus, we have discovered that by converting the NaOCl to HOCl and using it in the gas form the concentration needed for mold cidal activity and removal of mold stains is at least 13 times less than is recommended for liquid hypochlorite bleach!

The following examples are illustrative of solutions useful in accordance with the present invention and shall not be construed as being delimitive thereof.

EXAMPLE I 0.60% sodium hypochlorite in water
0.20 Molar KH$_2$PO$_4$ added and pH adjusted using aqueous H$_3$PO$_4$ or KOH to achieve pH of 6.6.

EXAMPLE II 0.060% sodium hypochlorite in water
0.20 Molar KH$_2$PO$_4$ added and pH adjusted using aqueous H$_3$PO$_4$ or KOH to achieve pH of 5.5.

EXAMPLE III 0.60% sodium hypochlorite in water
0.94 Molar lactic acid and pH adjusted using aqueous lactic acid or KOH to achieve pH of 5.3.

All of the solutions of Examples I–III are useful according to the invention for producing hypochlorous acid vapors which are to be distributed to an area that is to be treated for mold and reducing other contaminating bioburden that may include bacteria and their spores, yeast, and viruses. The hypochlorous acid concentration in the air must exceed 3×10$^{-7}$ grams/cubic centimeter for effective cidal action on mold-contaminated materials.

For Examples IV and IV below, visual inspection of the untreated control material plated onto an appropriate agar medium revealed numerous fungal colonies that were not inconsistent with members of the Stachybotrys, Penicillium, and Cladosporium genera.

EXAMPLE IV

Mold-contaminated fibrous ductwork lining was placed near an open container of hypochlorite solution at pH 5.5 and confined inside a larger closed container. The samples were incubated at ambient temperature, approximately 70° F. to 90° F. for about 24 hours. Subsequent microbial evaluations with this material streaked onto an appropriate agar medium indicated a high level of mold reduction compared to an untreated control sample. While strict quantitative microbiology techniques were not applied to this study, the biocidal potential of this solution was readily apparent.

EXAMPLE V

Mold-contaminated fibrous ductwork lining was placed near an open container of hypochlorite solution at pH of 5.5 and confined inside a larger closed container. The samples were incubated at ambient temperature, approximately 72° F. to 90° F. for about 24 hours. Subsequent microbial evaluations with this material streaked onto an appropriate agar medium indicated a high level of mold reduction compared to an untreated control sample. While strict quantitative microbiology techniques were not applied to this study, the biocidal potential of this solution was readily apparent. At this concentration of hypochlorous acid, the mycotoxin levels were judged to be reduced as evidenced by bleaching of the blacked background caused by the mold.

EXAMPLE VI

Into a vessel (1000 ml pyrex beaker) is poured 500 ml of a 1.00% aqueous solution of sodium hypochlorite. The pH of the solution is adjusted to 6.0 slowly using acetic acid. The air filter is removed from a home HVAC system and the beaker and its contents are then placed upon a flat surface behind the location at which the filter is housed. The air filter is replaced, and the air conditioning fan means is turned on, thus circulating the air through the ducts, including hypochlorous acid evolved from the vessel. The vessel is removed hourly and replaced by another beaker with fresh identical contents to the first.

The pH ranges noted herein have been are optimized for hypochlorous acid; however, if other hypohalides are used the pH ranges will need to be reoptimized using methods well known to those skilled in this art. In general, the optimum pH for the solution to be used in accordance with the present invention will be between the pKa of the hypohalide and two pH units below the pKa.

The preferred concentration range of hypohalous acid vapor for killing mold is any value in the range of between 1×10$^{-6}$ grams per cubic centimeter to 150×10$^{-6}$ grams per cubic centimeter. More preferably, concentration range of hypohalous acid vapor for killing mold is any value in the range of between 1×10$^{-6}$ grams per cubic centimeter to 75×10$^{-6}$ grams per cubic centimeter. It is most preferred that the concentration range of hypohalous acid vapor used for killing mold according to the present invention is any value in the range of between 3×10$^{-6}$ grams per cubic centimeter to 15×10$^{-6}$ grams per cubic centimeter.

Consideration must be given to the fact that although this invention has been described and disclosed in relation to certain preferred embodiments, obvious equivalent modifications and alterations thereof will become apparent to one of ordinary skill in this art upon reading and understanding this specification and the claims appended hereto. Accordingly, the presently disclosed invention is intended to cover all such modifications and alterations, and is limited only by the scope of the claims which follow.

What is claimed is:

1. A process for reducing and killing bioburden, including molds, bacteria and their spores, yeast, and viruses comprising the steps of:
    a) providing a vessel in an air conduit of an existing ventilation system inside a structure selected from the group consisting of a home or office building, the vessel containing an aqueous solution at a first pH level which comprises a compound from which a gaseous hypochlorous acid may be evolved upon adjustment of said aqueous solution to a second pH level;
    b) adjusting the pH of said aqueous solution from said first pH level to said second pH level so as to cause vapors comprising an hypochlorous acid to be evolved from said solution, and thus forming an actively-evolving solution;

c) causing an air current to exist in the ambient surroundings of said vessel from which said vapors are evolved so as to provide an air stream which contains a gaseous hypochlorous acid; and d) directing the flow of said air current to a location at which said bioburden is growing for an effective amount of time to kill said bioburden.

2. A process according to claim 1 further comprising the step of:

e) replenishing the source of compound from which a gaseous hypochlorous acid may be evolved after its depletion from said aqueous solution by virtue of the evolution of said gaseous hypochlorous acid from said solution.

3. A process according to claim 2 wherein said replenishing occurs after 10% of the compound from which a gaseous hypochlorous acid may be evolved has been depleted.

4. A process according to claim 1 wherein the concentration of said hypochlorous acid in said air current is in the range of between about 3 and 15 micrograms per cubic centimeter.

5. A process according to claim 1 wherein said location at which a mold colony is growing is a room within a dwelling selected from the group consisting of: a home residence dwelling, and an office building dwelling.

6. A process according to claim 5 wherein the concentration of said hypochlorous acid in said room is an effective concentration for killing molds.

7. A process according to claim 5 wherein the concentration of said hypochlorous acid in said room is in the range of between 3 and 15 micrograms per cubic centimeter of air.

8. A process according to claim 1 wherein said aqueous solution comprises ions selected from the group consisting of: hypoiodite ions, hypobromite ions, and hypochlorite ions.

9. A process according to claim 1 wherein said solution further comprises a corrosion inhibitor.

10. A process according to claim 9 wherein said corrosion inhibitor is selected from the group consisting of: di(alkali metal)phosphate, mono(alkali metal) phosphate, N,N'-dimethylethanolamine, morpholine, 2-mercaptobenzothiazole, 2,5-dimercapto-1,3,4-thiadiazole, sodium or potassium tolyltriazole, tolyltriazole, carboxybenzotriazole, quaternized imino imidazolines and quaternized amido imidazoles.

11. A process according to claim 1 wherein the aqueous solution further contains a pH buffer.

12. A process according to claim 11 wherein the buffer is selected from the group consisting of: phosphate buffers; sulfate buffers; acetic/acetate buffers; C1–C10 mono- and polycarboxylic acid buffers; substituted carboxylic acids such as lactic, ascorbic, and tartaric acid buffers; and unsaturated carboxylic acids such as maleic and furmaric buffers.

13. A process according to claim 1 wherein the first pH level of the aqueous solution is in the range of 8.0 to 14.0.

14. A process according to claim 1 wherein the second pH level of the aqueous solution is in the range of 3.0 and 7.9.

15. A process according to claim 1 wherein the pH of the contents of said vessel is adjusted by the addition of aqueous acid to said vessel.

16. A process according to claim 1 wherein the pH is adjusted from said first pH level to said second pH level by addition of an aqueous acidic substance selected from the group consisting of: hydrochloric acid, hydrobromic acid, hydriodic acid, sulfuric acid, acetic acid, and phosphoric acid.

17. A process according to claim 1 further comprising the step of monitoring the pH electronically.

18. A process according to claim 1 further comprising the step of monitoring the hypochlorous acid content of the air downstream of said vessel with an electrode.

19. A process according to claim 18 wherein the electrode is in electronic contact with a microprocessor.

20. A process according to claim 19 wherein said microprocessor is in contact with an automatic fluid dispenser which dispenser has an acidic aqueous effluent which is directed into said vessel.

21. A process according to claim 1 wherein the concentration of hypochlorous acid in said air conduit is caused to be in the range of between 3 and 15 micrograms per cubic centimeter of air by evolution of gaseous hypochlorous acid from said vessel.

22. A process for treating a ductwork which comprises the steps of:

a) providing a microprocessor having a means for inputting a signal and a signal outputting means;

b) providing an aqueous solution comprising an ionic form of an oxyhalogen compound which is buffered at a pH sufficient to liberate a gaseous hypochlorous acid, wherein said aqueous solution is disposed within an air conduit of an existing ventilation system inside a structure selected from the group consisting of a home or office building;

c) providing a means for conveying motion to the air which is in contact with the solution so as to form a first air stream;

d) causing the first air stream to be directed to a surface upon which a living mold resides, at an effective rate for causing inhibition of the growth of the mold; and e) monitoring the concentration of the hypochlorous acid content of the first air stream by means of an electrochemical probe connected to the means for inputting a signal to the microprocessor, wherein the microprocessor controls the concentration of the hypochlorous acid in the first air stream to be any value in the range of between $3\times10^{-6}$ grams/cubic centimeter and $15\times10^{-6}$ grams/cubic centimeter.

* * * * *